(12) United States Patent
Shaw et al.

(10) Patent No.: US 9,440,033 B2
(45) Date of Patent: Sep. 13, 2016

(54) FLUID FLOW CONTROL DEVICE WITH RETRACTABLE CANNULA

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Leonard, TX (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 755 days.

(21) Appl. No.: 13/902,564

(22) Filed: May 24, 2013

(65) Prior Publication Data

US 2013/0261551 A1 Oct. 3, 2013
US 2016/0166778 A9 Jun. 16, 2016

Related U.S. Application Data

(60) Division of application No. 13/470,855, filed on May 14, 2012, now Pat. No. 8,469,927, which is a continuation of application No. 12/136,462, filed on Jun. 10, 2008, now abandoned.

(51) Int. Cl.
*A61M 5/50* (2006.01)
*A61M 5/158* (2006.01)
(Continued)

(52) U.S. Cl.
CPC .............. *A61M 5/50* (2013.01); *A61M 5/158* (2013.01); *A61M 5/3257* (2013.01); *A61M 5/3232* (2013.01); *A61M 25/0631* (2013.01); *A61M 25/0637* (2013.01)

(58) Field of Classification Search
CPC .. A61M 5/321; A61M 5/322; A61M 5/3221; A61M 5/3232; A61M 5/3234; A61M 5/50; A61M 2005/3223; A61M 2005/3224; A61M 2005/3226; A61M 2005/3227; A61M 2005/3228; A61M 2005/323; A61M 2005/3231; A61M 2005/3235; A61M 2005/3236; A61M 2005/3238; A61M 2005/3239; A61M 2005/3241; A61M 2005/342; A61M 525/0631
See application file for complete search history.

(56) References Cited

U.S. PATENT DOCUMENTS 4,624,393 A 11/1986 Lopez
4,813,426 A 3/1989 Haber et al.
(Continued)

FOREIGN PATENT DOCUMENTS

EP 0479303 4/1992
EP 1161962 12/2001
(Continued)

*Primary Examiner* — Kami A Bosworth
(74) *Attorney, Agent, or Firm* — Ross Barnes LLP; Monty L. Ross; Robin L. Barnes

(57) ABSTRACT

A device having a housing; a cannula projecting forwardly from the housing; a connector useful for attaching the device to a fluid source or receptacle; a fluid flow path establishing fluid communication between the cannula and the connector; a retraction mechanism biasing the cannula away from its projecting position; and an actuator supported by the housing and configured to modify the fluid flow path so as to terminate fluid flow through the device, seal off the fluid flow path, and release the retraction mechanism to retract the cannula into the housing. The subject device is particularly preferred for use in the medical field, for example, as part of an infusion set or as a collection device for blood, or other fluids or flowable matter.

6 Claims, 12 Drawing Sheets

(51) Int. Cl.
*A61M 5/32* (2006.01)
*A61M 25/06* (2006.01)

(56) References Cited

U.S. PATENT DOCUMENTS

| | | |
|---|---|---|
| 5,423,758 A | 6/1995 | Shaw |
| 5,685,863 A | 11/1997 | Botich et al. |
| 5,779,679 A | 7/1998 | Shaw |
| 5,957,887 A | 9/1999 | Osterlind et al. |
| 6,039,713 A | 3/2000 | Botich et al. |
| 6,063,040 A | 5/2000 | Owen et al. |
| 6,210,371 B1 | 4/2001 | Shaw |
| 6,277,102 B1 * | 8/2001 | Carilli ............. A61M 5/1782 604/240 |
| 8,469,927 B2 | 6/2013 | Shaw et al. |
| 2002/0068907 A1 | 6/2002 | Dysarz |
| 2002/0165501 A1 | 11/2002 | Yang |
| 2003/0078540 A1 | 4/2003 | Saulenas et al. |
| 2003/0181871 A1 | 9/2003 | Wilkinson et al. |
| 2004/0019329 A1 | 1/2004 | Erskine |
| 2004/0204688 A1 | 10/2004 | Lin et al. |
| 2005/0288607 A1 | 12/2005 | Konrad |
| 2006/0155244 A1 | 7/2006 | Popov |
| 2006/0235354 A1 | 10/2006 | Kaal et al. |
| 2009/0306601 A1 | 12/2009 | Shaw |

FOREIGN PATENT DOCUMENTS

| | | |
|---|---|---|
| WO | WO9924092 | 5/1999 |
| WO | WO03099349 | 5/2003 |

* cited by examiner

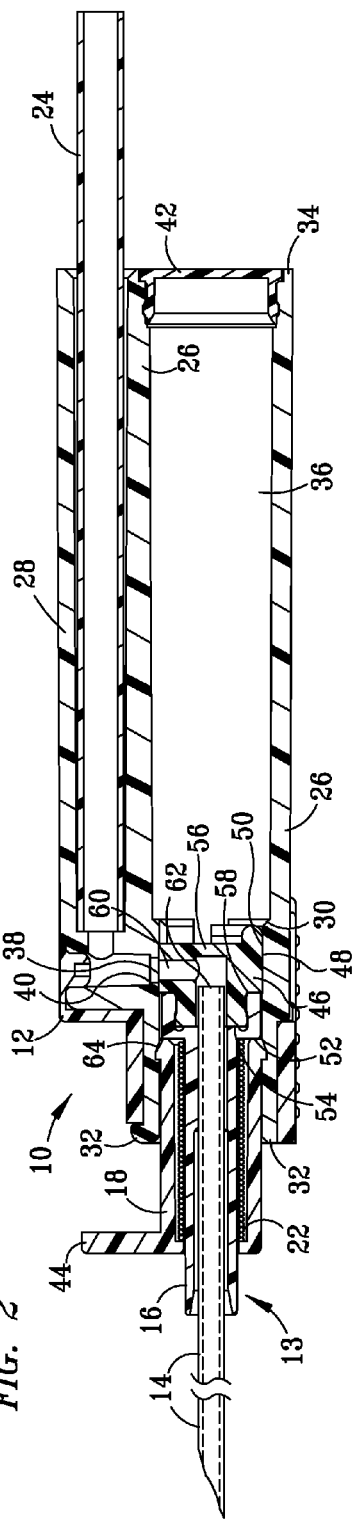
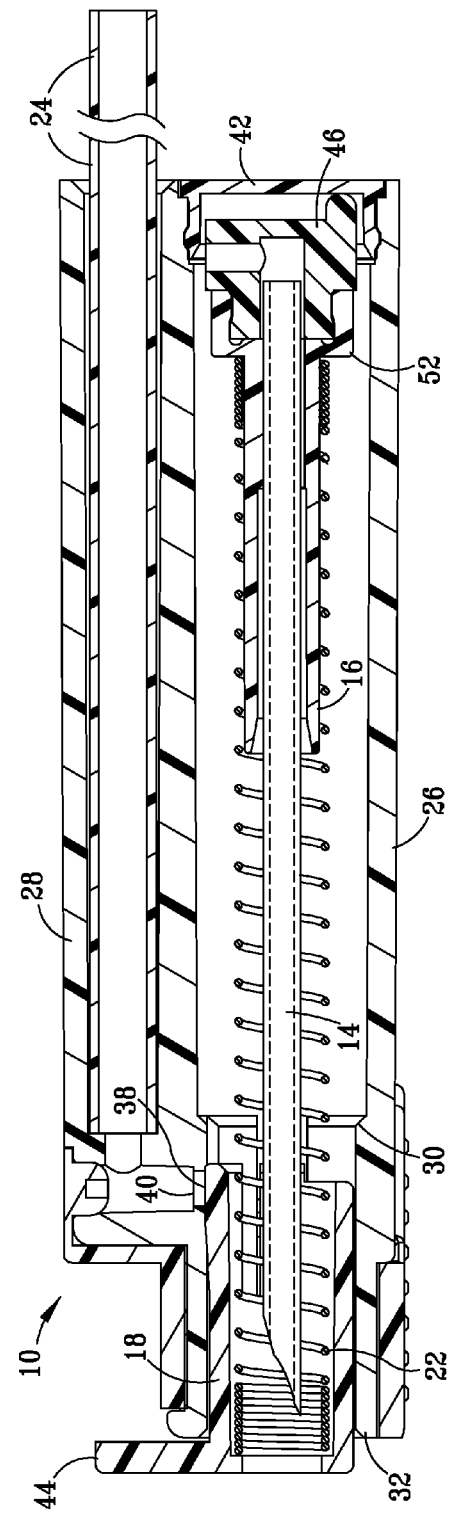

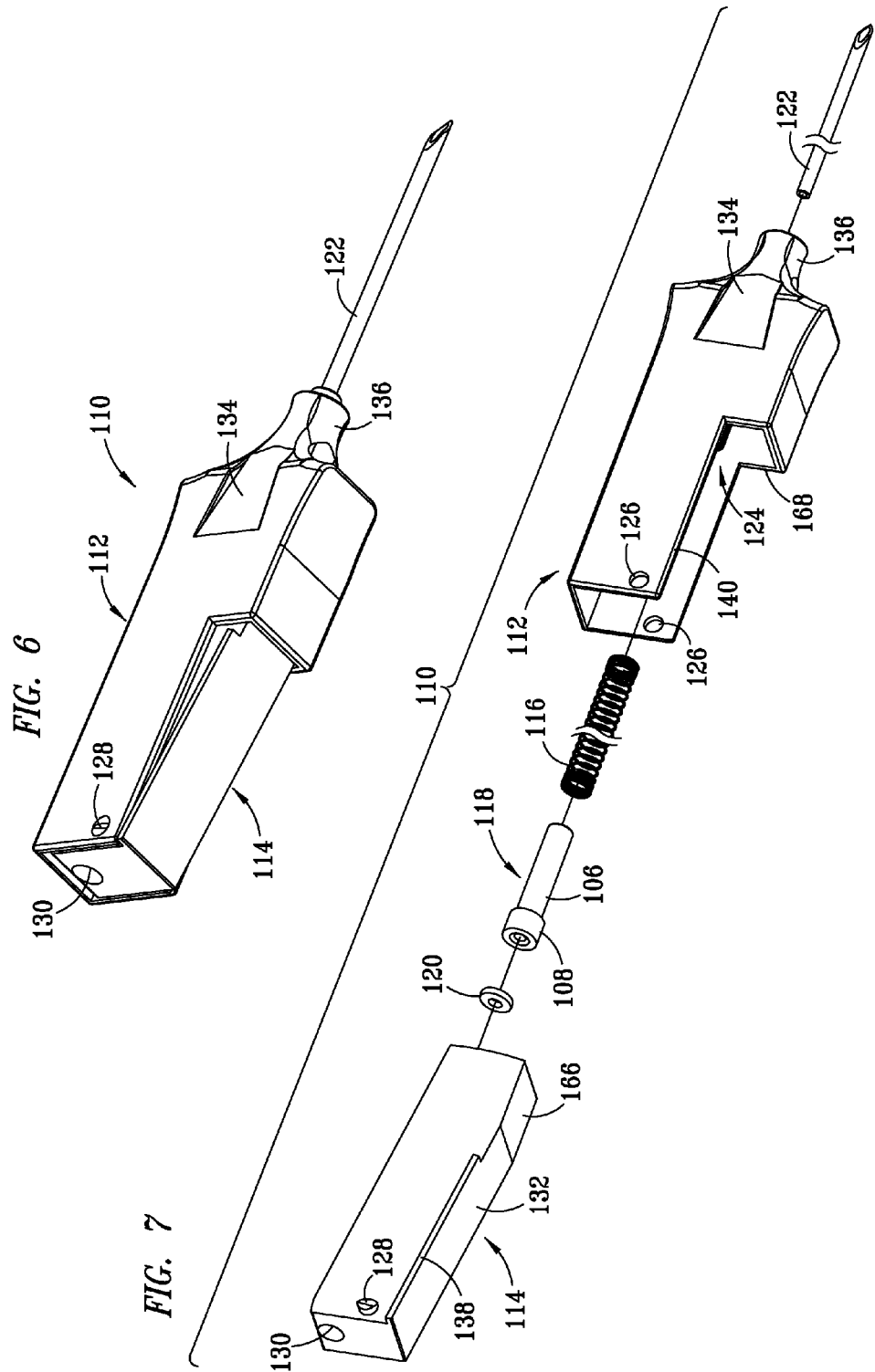

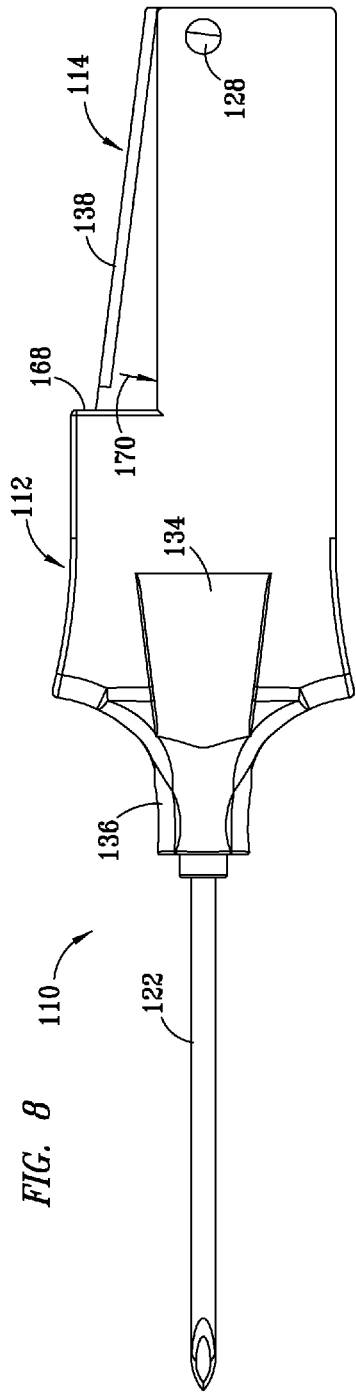
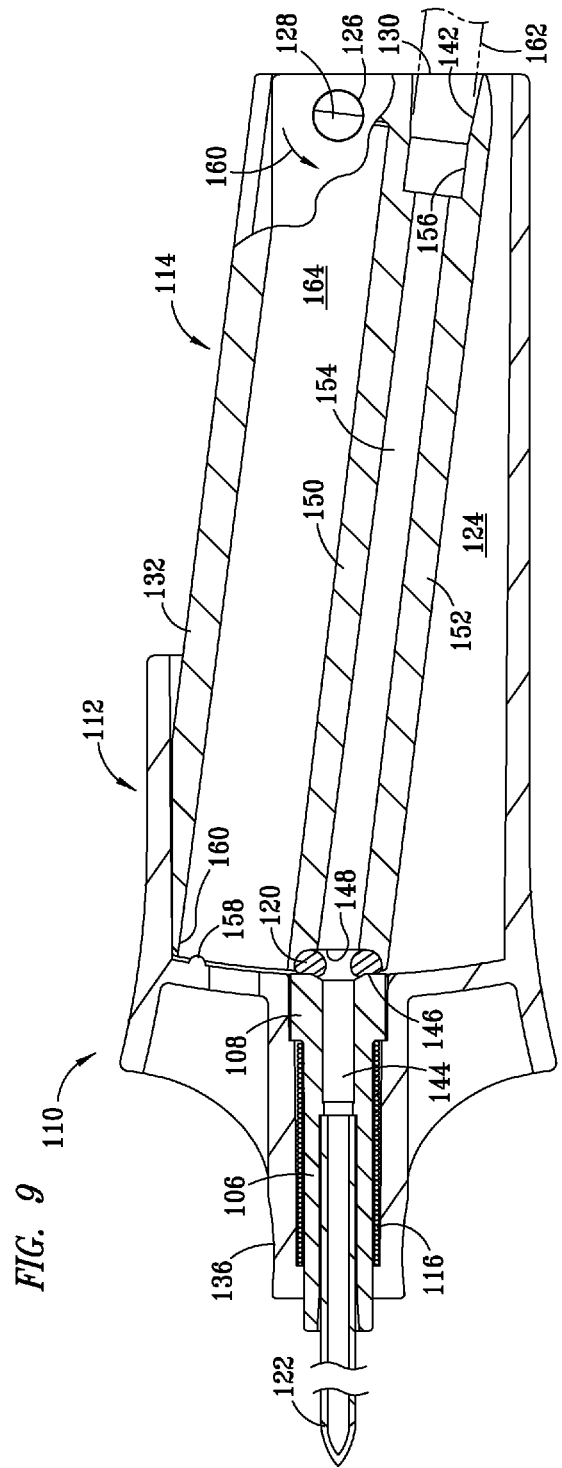
FIG. 8
FIG. 9

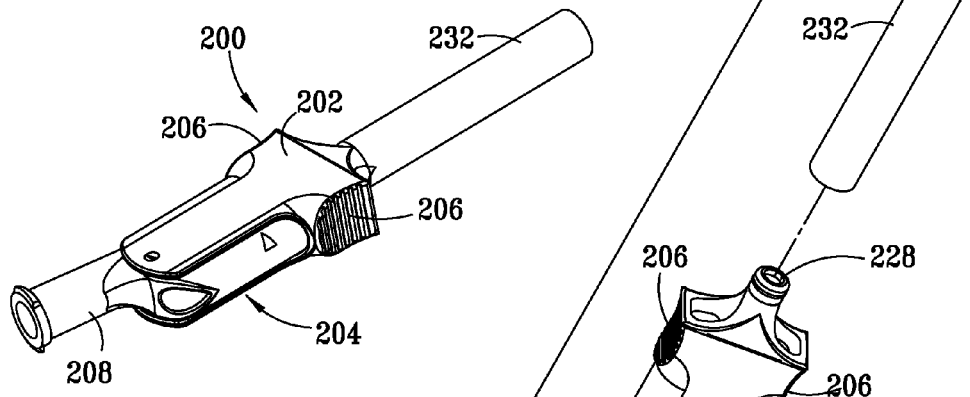
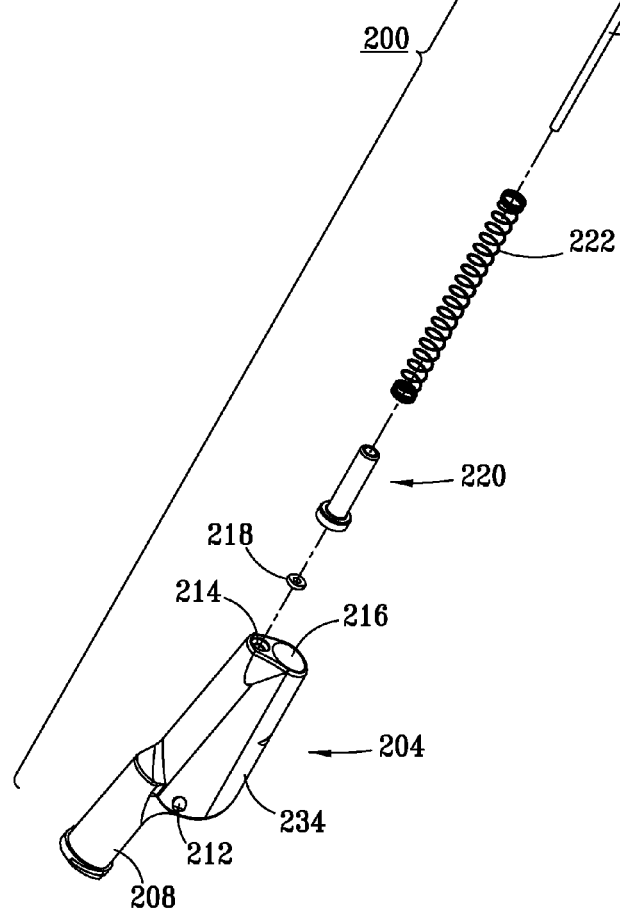
FIG. 11
FIG. 12

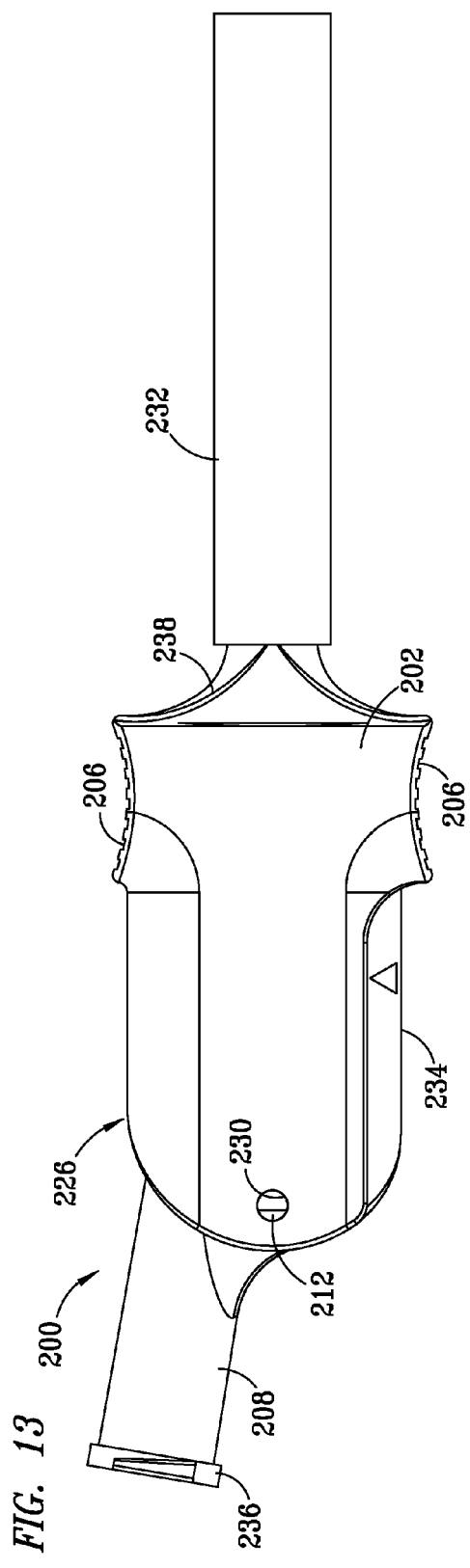
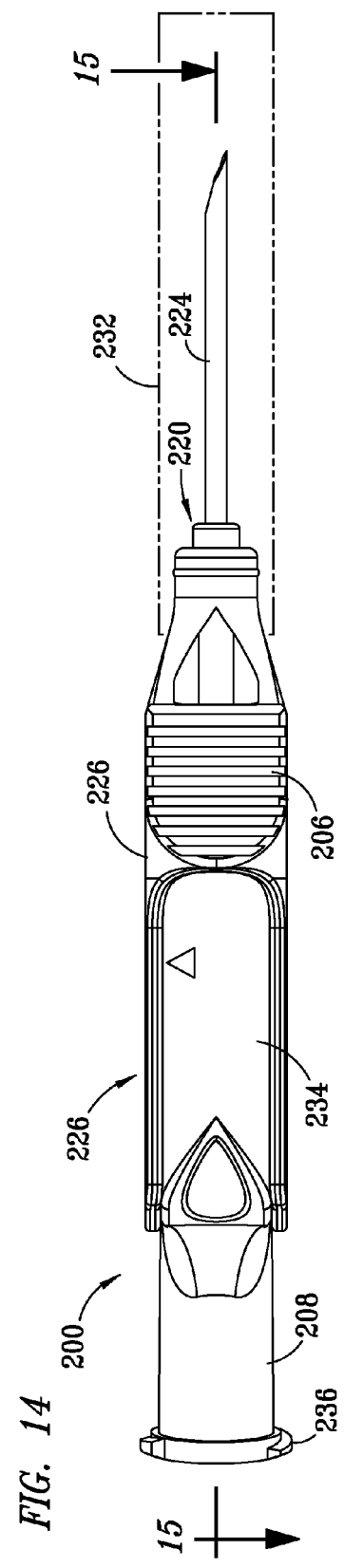

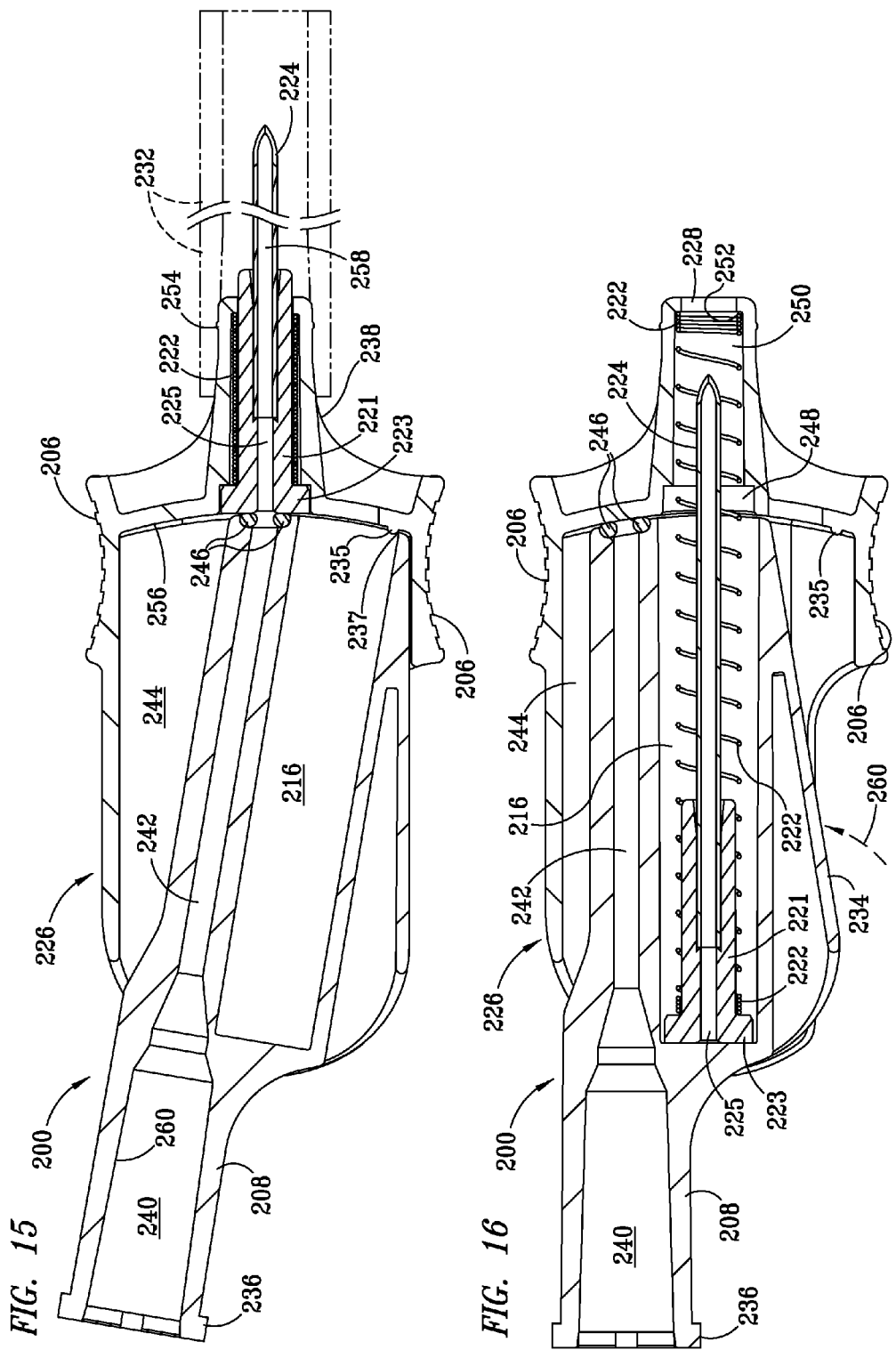

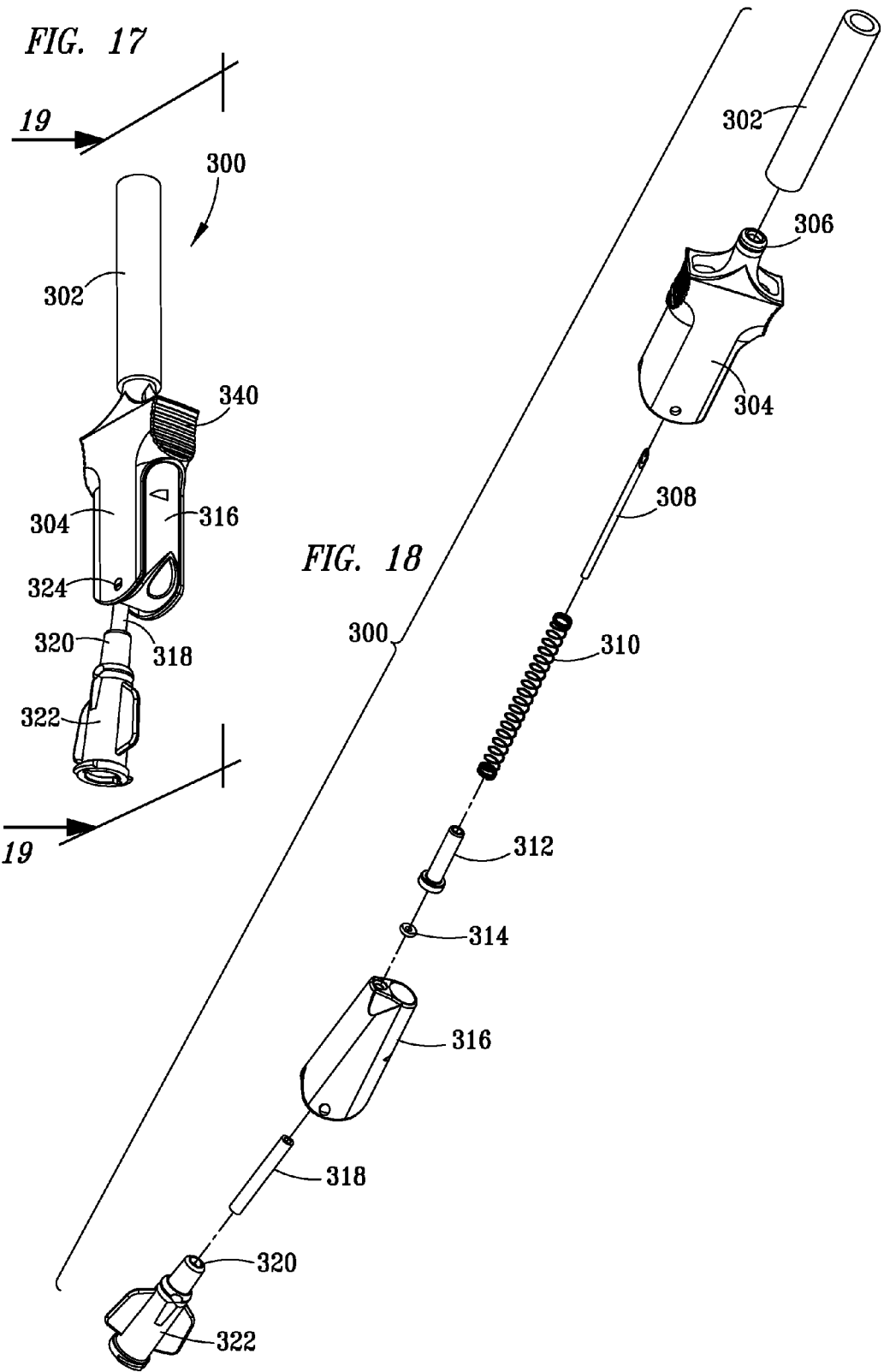

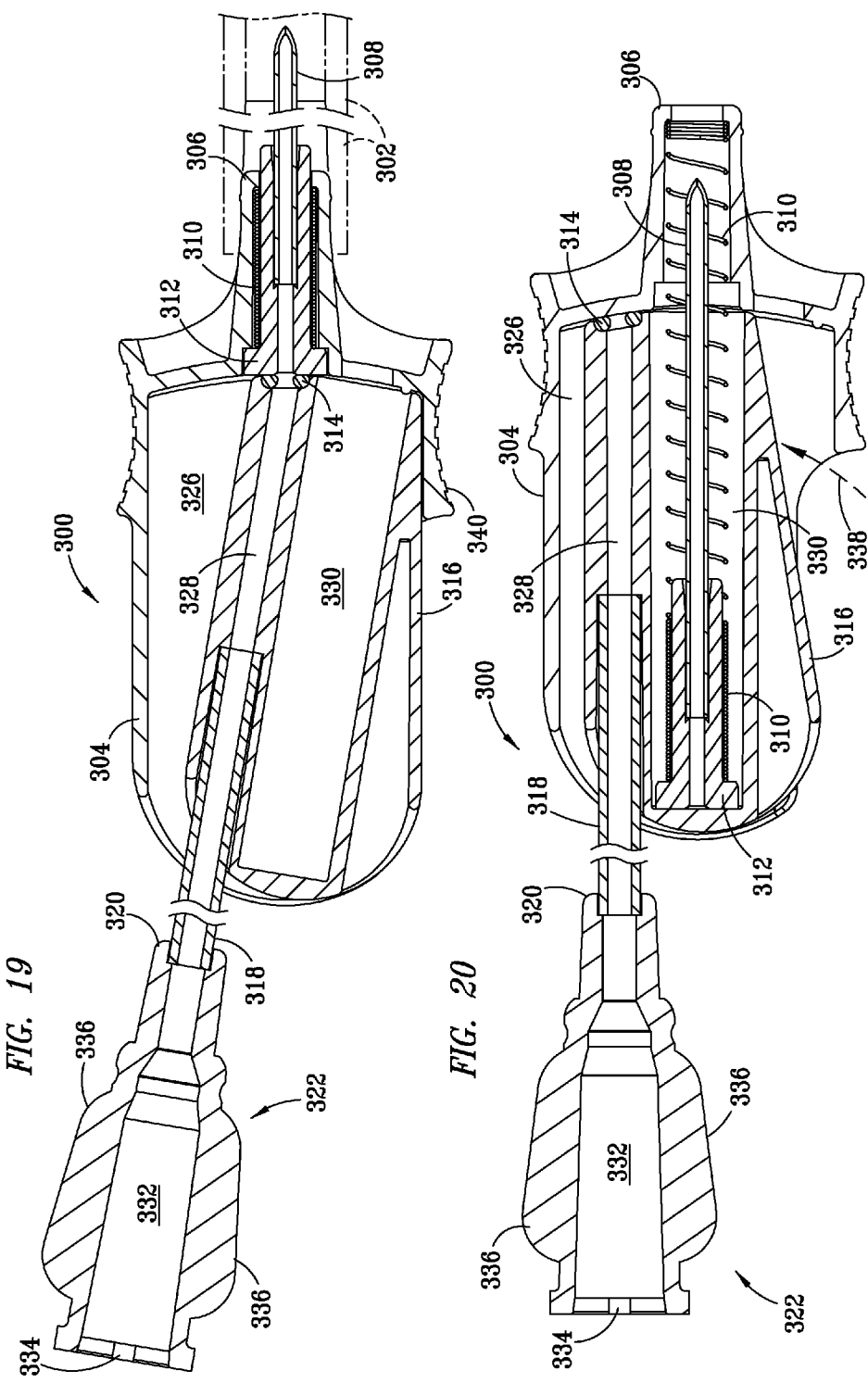

FLUID FLOW CONTROL DEVICE WITH RETRACTABLE CANNULA

CROSS REFERENCE TO RELATED APPLICATION

This divisional application claims priority to U.S. patent application Ser. No. 13/470,855, filed on May 14, 2012, which is a continuation of U.S. patent application Ser. No. 12/136,462, filed on Jun. 10, 2008, now abandoned.

BACKGROUND OF THE INVENTION

1. Field of the Invention

This invention relates to a fluid flow control device and, in a preferred embodiment, to a medical device having a cannula, often a needle, that is insertable into a patient for use in infusing, collecting or extracting fluids. One aspect of the invention relates to a medical device having an actuator that is manipulated to modify a fluid flow path between the cannula and an external fluid source or receptacle following the infusion or extraction. Another aspect of the invention relates to a mechanism that functions as a clamp when attached to a fluid flow line. Another aspect of the invention relates to a mechanism that retracts the cannula inside the device to prevent accidental needlesticks following use and to prevent reuse of the contaminated cannula. Although the subject invention is particularly preferred for use in intravascular ("IV") applications, it can also be used beneficially, for example, in epidural, intraosseous and intraocular applications, and with any body fluid.

2. Description of Related Art

Intravascular ("IV") infusion sets are well-known in the art for delivering fluids and/or medications to a patient by means of a cannula connected to tubing. IV infusion devices frequently have attached wings that facilitate handling during insertion of the cannula, help stabilize the device, and can be secured to limit movement of the device during use. Blood collection devices operate on the same principle, but in reverse. Blood is collected from a vein or artery through a cannula that is connected through the body of the device to a blood collection receptacle. Following use of a conventional infusion or fluid collection system, the cannula is contaminated with blood and/or other bodily fluid, and care must be taken to avoid reusing the device and to avoid accidentally sticking either healthcare workers or patients, and thereby spreading blood-borne pathogens. The use of caps or covers that must be replaced over the cannula after withdrawal from a patient are not a satisfactory solution because they increase the risk for an accidental stick, or can become loose and fall off, thereby again exposing the contaminated cannula.

U.S. Pat. No. 5,779,679 to Shaw, entitled "Winged IV Set With Retractable Cannula," and U.S. Pat. No. 6,210,371 to Shaw, entitled "Winged IV Set," both disclose an IV infusion set with a retractable cannula. In both of these patents, the retractable cannula is held by a retraction member having a tubing connector on its back end portion that establishes fluid communication between the cannula and an IV tube. The retraction member is held in its non-retracted position against the force of a compressed spring by a pair of releasable latches disposed on opposite sides of the housing. Once the latches are released, the spring forces the retraction member, and consequently the cannula, back into the housing. However, because an IV tube is connected directly to the retraction member, retraction of the cannula causes the IV tube to move rearwardly as well. If the tube is not free to move rearwardly during retraction, the retraction member and the cannula may not be fully retracted.

An infusion and fluid collection device are needed in which the cannula can be retracted without causing or relying upon rearward movement of the connected tubing, and in such manner that the device is rendered non-reusable and that the fluid flow path is interrupted, relocated and sealed off in conjunction with retraction of the cannula.

SUMMARY OF THE INVENTION

The apparatus of the invention comprises a device that is particularly well suited for use in the medical field, but is not necessarily limited to medical use. According to one preferred embodiment of the invention, a medical device is disclosed that has a cannula and can be configured and used for fluid injection, infusion or extraction. Depending upon its configuration, the subject device can be used, for example: As part of an infusion set or as a collection device for venous or arterial blood; for other body fluids such as spinal fluid, cerebral fluid, amniotic fluid, and the like that are well known to healthcare workers; or for solid matter contained in suspensions or slurries such as, for example, medications, lipids or bone marrow. When the device is used for infusing fluids or medication, the fluid source can be, for example, an IV drip bag or a syringe. When the device is used for collecting blood, the fluid receptacle can be, for example, a blood collection bag, an evacuated tube or a syringe. When the device is attached to a fluid flow line, it can also be used as a clamp. Prior to retraction of the cannula, the device prevents fluid leakage into or out of the fluid flow path. The cannula is typically a needle having a front end that is beveled to facilitate insertion into tissue or into another medical device such as a port.

According to one embodiment of the invention, the device comprises an offset fluid flow path and a retraction chamber fixed in a position that is in-line with the cannula. Retraction is initiated by an actuator that can be repositioned axially in relation to the cannula, thereby also blocking the fluid flow path.

According to another embodiment of the invention, the device comprises an in-line fluid flow path and an offset retraction cavity. Retraction is initiated by an actuator that can be repositioned laterally in relation to the cannula, thereby blocking and sealing off the fluid flow path.

According to another embodiment of the invention, the device comprises an in-line fluid flow path and an offset retraction chamber. Retraction is initiated by an actuator that can be repositioned arcuately in relation to the cannula, thereby blocking and sealing off the fluid flow path.

According to a preferred embodiment of the invention, a device is disclosed that preferably comprises a housing; a cannula projecting forwardly from the housing; a connector useful for attaching the device to a fluid source or receptacle; a fluid flow path establishing fluid communication between the cannula and the connector; a retraction mechanism biasing the cannula away from its projecting position; and an actuator supported by the housing and configured to modify the fluid flow path so as to terminate fluid flow through the device, seal off the fluid flow path, and release the retraction mechanism to retract the cannula into the housing. Laterally extending finger grips and/or stabilization wings with finger pads are desirably provided to facilitate manipulation of the device by a user, to resist rolling of the device on an underlying surface, and to provide surfaces that can be secured to a patient during use.

According to another preferred embodiment of the invention, the actuator portion of the device comprises two elongate, most preferably cylindrical, cavities, including one cavity that defines a portion of the fluid flow path and another that is a retraction cavity configured to receive a portion of the retraction mechanism and cannula following retraction. The retraction mechanism preferably comprises a holder for the needle or cannula, and a biasing member such as a compression spring. The actuator is preferably movable by the user from a first position to a second position to modify the fluid flow path by interrupting, displacing, redirecting or reconfiguring at least part of the path, thereby cutting off fluid flow along the original flow path through the device. At least part of the actuator is either slidably mounted or rotatably, most preferably pivotally, connected inside the housing. Movement of the actuator from the first position to the second position also desirably releases the retraction mechanism, allowing the biasing member to force the cannula holder and at least part of the cannula back inside the retraction cavity, and to force all of the cannula back inside the housing to prevent accidental needle sticks and to prevent reuse of the device. The use of devices having retractable needles, the avoidance of accidental needlesticks and disabling the device to prevent reuse are important to significantly reducing the spread of disease by blood-borne pathogens to healthcare workers, other patients, and those who may handle such devices following use.

BRIEF DESCRIPTION OF THE DRAWINGS

The apparatus of the invention is further described and explained in relation to the following figures of the drawings wherein:

FIG. 2 is a cross-sectional side elevation view taken along line 2-2 of FIG. 1;

FIG. 3 is an enlarged view of the device of FIG. 2 following interruption of the fluid flow path and retraction of the cannula;

FIG. 6 is a perspective view of another embodiment of the invention having an interruptable fluid flow path, a retractable cannula projecting forwardly out of the housing, and a pivotable actuator;

FIG. 7 is an exploded perspective view of the embodiment of FIG. 6;

FIG. 8 is an enlarged top plan view (oppositely directed) of the embodiment of FIG. 6;

FIG. 9 is an enlarged cross-sectional plan view, partially broken away, of the embodiment of FIG. 8, with the cannula projecting forwardly and a tubing segment (shown in phantom outline) disposed in fluid communication with the fluid flow path through the actuator, cannula holder and cannula;

FIG. 11 is a perspective view of another embodiment of the invention having an interruptable fluid flow path, a retractable cannula projecting forwardly out of the housing (shown covered by a protective guard), and an actuator pivotably connected to the housing;

FIG. 12 is an exploded perspective view of the embodiment of FIG. 11;

FIG. 13 is an enlarged top plan view of the embodiment of FIG. 11;

FIG. 14 is a front elevation view of the embodiment of FIG. 13, with the protective cover shown in phantom outline;

FIG. 15 is an enlarged cross-sectional plan view, partially broken away, of the embodiment of FIG. 13, with the cannula projecting forwardly and the protective cover shown in phantom, showing the fluid flow path through the cannula, cannula holder and actuator;

FIG. 16 is a cross-sectional plan view of the embodiment of FIG. 15 following interruption of the fluid flow path and retraction of the cannula into the retraction cavity;

FIG. 17 is a perspective view of another embodiment of the invention having an interruptable fluid flow path that is particularly useful with liquid fluids, a retractable cannula projecting forwardly out of the housing (hidden from view by a removable protective cover), and an actuator pivotably connected to the housing;

FIG. 18 is an exploded perspective view of the embodiment of FIG. 17;

FIG. 19 is an enlarged cross-sectional plan view, partially broken away, of the embodiment of FIG. 17, with the cannula projecting forwardly and the protective cover shown in phantom outline, and showing the fluid flow path through the cannula, cannula holder, actuator and Luer connector set; and FIG. 20 is a cross-sectional plan view of the embodiment of FIG. 19 following interruption of the fluid flow path and retraction of the cannula into the retraction cavity.

DESCRIPTION OF THE PREFERRED EMBODIMENTS

Figure 1:
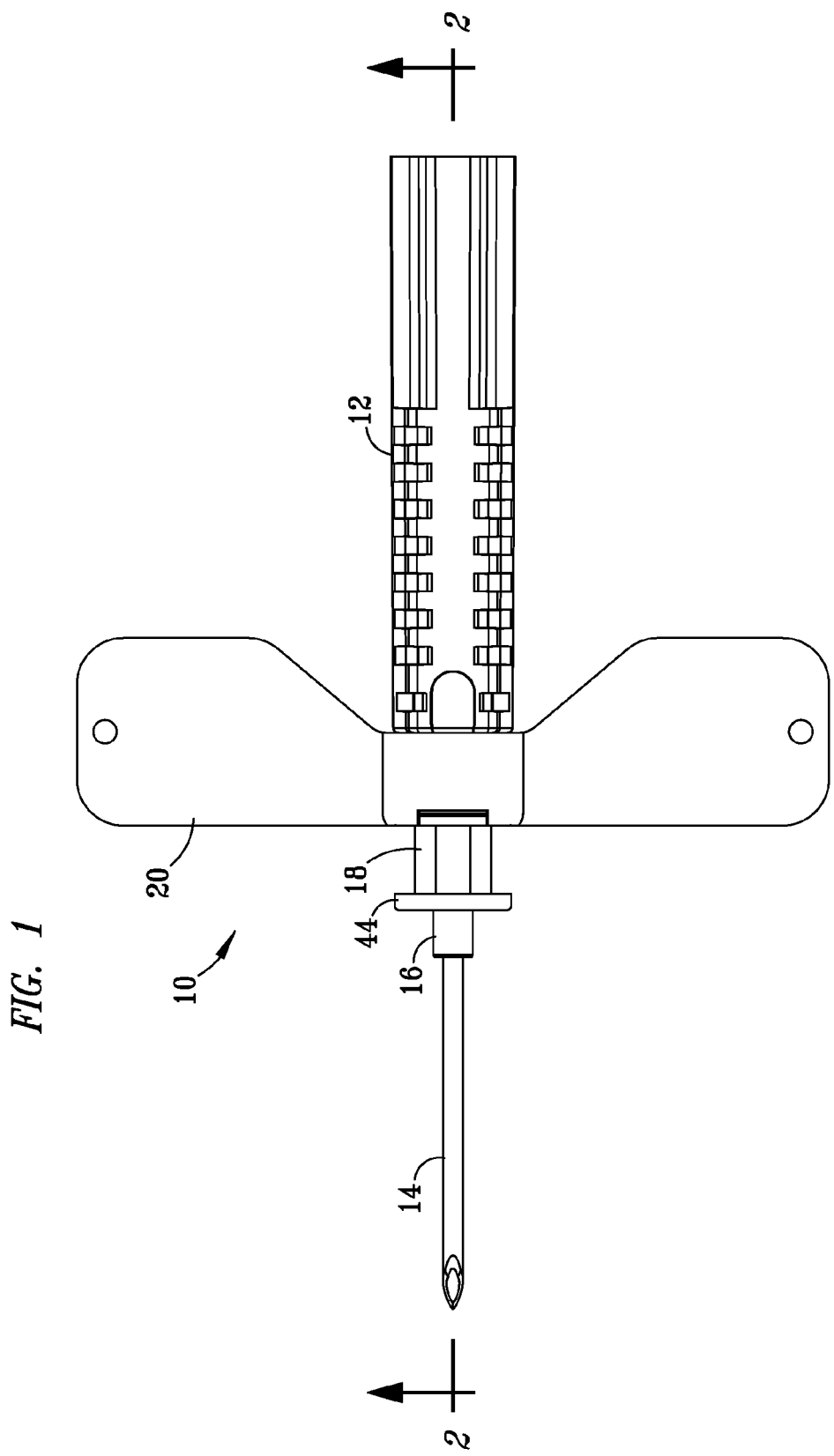
FIG. 1 is a front elevation view of an embodiment of the invention having an interruptable fluid flow path, a retractable cannula projecting forwardly out of the housing, a rearwardly slidable actuator, and stabilization wings.

Referring to FIG. 1, device 10 can be used, for example, as part of a medical apparatus for collecting blood, blood gases or other bodily fluids from a patient, or for infusing a patient with fluids of the type typically administered intravenously or otherwise. As shown, device 10 comprises housing 12 and forwardly projecting cannula 14 attached to cannula holder 16, which is more visible in FIGS. 2 and 3. Prior to use of device 10, the beveled point of cannula 14 is desirably shielded by a protective cover. Actuator 18 is slidably supported by housing 12 and comprises a plurality of opposed flexible latches that secure the end opposite handle 44 inside housing 12. Handle 44 at the front of actuator 18 facilitates manual manipulation of actuator 18 relative to housing 12 to terminate fluid flow through device 10 and initiate retraction of cannula 14 inside housing 12 as described in greater detail below.

Optional stabilization wings 20 extend laterally from housing 12 and facilitate handling of device 10 by the user. When used, wings 20 also provide a surface that will restrict rotation of housing 12 when device 10 is secured to a patient using tape, sutures, or other similarly effective means. After a desired volume of fluid has been administered to or withdrawn from a patient as therapeutically prescribed, the fluid flow through cannula 14 can be terminated and cannula 14 can be retracted inside housing 12 by applying rearwardly directed manual pressure to the front side of handle 44 of actuator 18 while simultaneously grasping housing 12. If desired, cannula 14 can be retracted into housing 12 without first withdrawing it from the patient. Usage of device 10 and retraction of cannula 14 are discussed more fully below in relation to FIGS. 2 and 3.

Referring to FIG. 2, device 10 is shown without the optional stabilization wings attached. Housing 12 of device 10 comprises two elongated portions including lower section 26 and upper section 28. Lower section 26 further comprises smaller diameter front end 32 and a larger diameter back end 34 with transition zone defined by shoulder 30 disposed between front end 32 and back end 34. Upper section 28 extends rearwardly from a point above shoulder 30 to an open back end above back end 34 of lower section 26, and comprises a longitudinal bore that serves as a connector into which tubing segment 24 is insertable. The end of tubing segment 24 is desirably maintained inside upper section 28 of housing 12 by any suitable means such as, for example, frictional engagement or by using a clamping device, adhesive, or the like. Depending upon the desired use of device 10, tubing segment 24 can be of any desired length that is suitable for connecting device 10 to a fluid source, such as an IV bag, or to a fluid receptacle, such as a blood collection system. Lower section 26 preferably further comprises a retraction cavity 36 disposed between back end 34 and transition zone shoulder 30. As shown, back end 34 of retraction cavity 36 comprises an opening that is closed by end cap 42. Lower section 26 further comprises aperture 38 disposed in the top wall, slightly forward of transition zone shoulder 30. Hole 38 aligns with hole 40 in the bottom of upper section 28, and the alignment of holes 38, 40 helps establish a fluid flow path between cannula 14 and tubing segment 24.

The opening at front end 32 of lower section 26 is closed by slidably engaged tubular actuator 18, which comprises handle 44 extending upwardly from the front edge. Actuator 18 is movable from a first position, where handle 44 is spaced apart from front end 32 of lower section 26, to a second position, where handle 44 abuts and is adjacent to front end 32 of lower section 26. Actuator 18 is desirably sized lengthwise to extend into lower section 26 of housing 12 a sufficient distance to cover and close hole 38 in lower section 26 when actuator 18 is moved to the second position abutting against front end 32. Actuator 18 also desirably comprises a pair of diametrically opposed latches extending outwardly from the rear end of actuator 18. As sliding end cap 18 is moved towards its second position, the latches slide over and engage a projection shoulder on the inside wall of lower section 26, thereby locking actuator 18 in its second position and preventing its removal from housing 12.

Retraction mechanism 13 supports cannula 14 and comprises cannula holder 16, cannula holder plug 46, and spring 22. Following installation of actuator 18 in the front of lower section 26, cannula holder 16, spring 22 and cannula holder plug 46 are desirably preassembled and inserted into lower section 26 through the opening in back end 34 and through retraction cavity 36. Prior to insertion, resilient cannula holder plug 46 is desirably inserted into frictional engagement with a recess inside the larger diameter section 58 of cannula holder 16. Spring 22 is desirably placed over the smaller diameter front section of cannula holder 16, where it slides rearwardly into abutting engagement with annular shoulder 52. The assembled unit is then oriented so that fluid passageway 60 is aligned with aperture 38 in the top wall of lower section 26, and advanced past transition zone shoulder 30. As the forwardly extending tip of cannula holder 16 projects forwardly of actuator 18, spring 22 seats against the annular shoulder inside the front opening of actuator 18 and is compressed to the position shown in FIG. 2. Actuator 18 resists the force of the compressed spring and is prevented from moving forwardly away from housing 12 under the spring force by the resilient latches securing actuator 18 to housing 12 as previously described. This configuration of elements allows cannula 14 to be in fluid communication with tubing 24, as fluid flows through hollow cannula 14 and cannula holder 16 into cannula holder plug 46, through hole 60 in the top of cannula holder plug 46, through hole 38 in top of retraction cavity housing 26, through hole 40 in the bottom of tubing assembly housing 28 and into tubing 24. Similarly, fluid can flow in the opposite direction and pass from tubing 24, through aligned holes 40, 38 and 60 and out cannula 14. Rear end cap 42 is installed in the open end of lower section 26 following installation of cannula 14 and cannula holder plug 46, and is frictionally held inside rear end 34 of lower section 26.

Although cannula 14 can be secured in fixed relation to cannula holder 16 prior to insertion of retraction mechanism 13 into housing 12, cannula 14 is desirably inserted into the bore of projecting tip of cannula holder 16 after cannula holder 16 is installed inside housing 12. As seen in FIG. 2, the opening at the forwardly extending end of cannula holder 16 is tapered to facilitate the insertion and attachment of cannula 14. Cannula 14 can be frictionally held inside the bore of cannula holder 16 but is desirably attached in fixed relation to cannula holder 16 using glue or any other similarly effective means known to those of ordinary skill in the art. The open portion of the beveled point of cannula 14 desirably faces upwardly to facilitate insertion into a patient. As shown in FIG. 2, open back end 62 of hollow cannula 14 extends through back end 58 of cannula holder 16 into open front section 54 of cannula holder plug 46. It should be appreciated, however, that cannula 14 needs only extend into cannula holder 16 a sufficient distance to facilitate reliable engagement between them.

When device 10 is assembled as described above, compressed spring 22, or any other similarly effective biasing means, biases cannula 14 and cannula holder 16 rearwardly. The frictional holding force exerted against inside surface 50 of the smaller diameter front portion of lower section 26 by cannula holder plug 46 should be great enough to resist the biasing force exerted against annular shoulder 52 by spring 22 in combination with the force exerted back against cannula holder plug 46 through cannula 14 and cannula holder 16 during insertion of cannula 14 into a patient. Otherwise, cannula 14 could retract prematurely without movement of actuator 18 relative to housing 12.

When the fluid infusion or extraction procedure is complete and retraction of cannula 14, the user can initiate retraction by applying rearwardly directed pressure to handle 44 while maintaining housing 12 in a stationary position, either by gripping its textured outside surface portion (visible in FIG. 1) or by pressing down on the optional wings (likely already secured to the patient). The manual pressure applied to handle 44 causes actuator 18 to move backwards relative to housing 12. Desirably, retraction is initiated while the cannula, typically a needle, is still inserted in the patient. As actuator 18 moves backwards, cannula holder 16 and cannula holder plug 46 are also forced backwards due to the contact between back end 64 of actuator 18 and annular shoulder 52 of cannula holder 16. It can be observed in FIG. 2 that back end 64 of actuator 18 abuts the adjacent portion of forwardly facing annular shoulder 52 of cannula holder 16, while the rear end of that part of actuator 18 as depicted beneath spring 22 is slightly separated from annular shoulder 52. This slight separation causes the rearwardly directed force exerted by the user on handle 44 to be concentrated against one side of annular shoulder 52 rather than being evenly distributed around the circumference, and is believed to reduce the manual force required to initiate retraction.

Referring to FIG. 3, in response to the rearward movement of actuator 18, cannula holder plug 46 passes through the transition zone (past shoulder 30) and into larger diameter retraction cavity 36 of lower section 26. As cannula holder plug 46 moves, the friction force between outside surface 48 of cannula holder plug 46 and inside wall 50 of lower section 26 is reduced, and as cannula holder plug 46 passes the transition zone and enters retraction cavity 36, the frictional holding force is completely eliminated. At the point where the frictional holding force is sufficiently reduced by the combined finger force of the user as applied through handle 44 of actuator 18 and the biasing force of compressed spring 22, spring 22 forces cannula holder 16 and cannula holder plug 46 backwards into retraction cavity 36, thereby simultaneously causing cannula holder 16 to draw the beveled tip of cannula 14 inside housing 12. It will be apparent to those of skill in the art upon reading this disclosure that actuator 18 should be long enough that its range of travel relative to housing 12 is sufficient to force cannula holder plug 46 past shoulder 30.

As shown in FIG. 3, following retraction, cannula holder plug 46 desirably abuts, or nearly abuts, rear end cap 42 of lower section 26. Lower section 26 is desirably sized such that the entirety of cannula 14 is contained within lower section 26 and does not protrude from front end 32. After retraction, the top edge of actuator 18 blocks the fluid flow path between cannula 14 and hole 38 in the top of lower section 26. This prevents fluid from escaping tubing 24 that is still connected to upper section 28 of housing 12.

Figure 4:
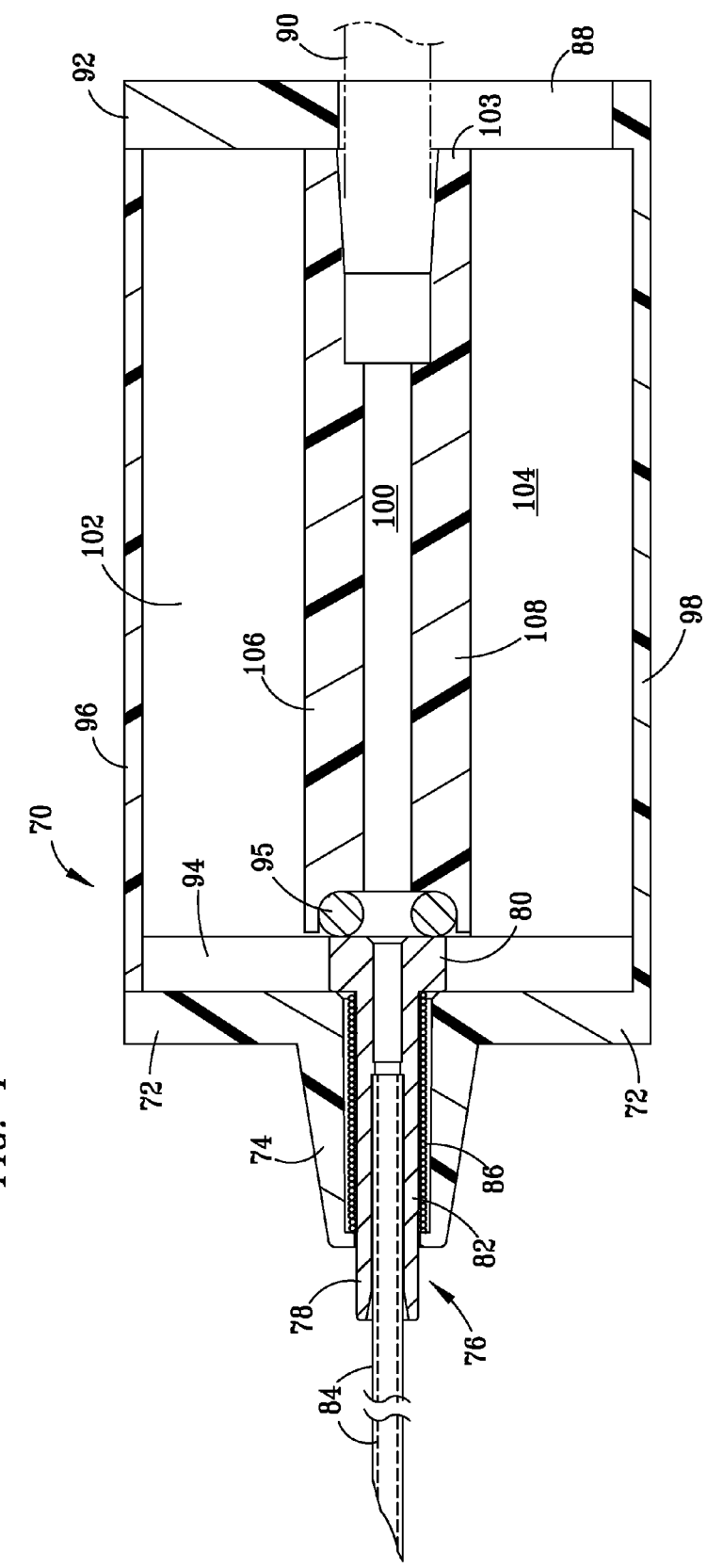
FIG. 4 is a cross-sectional front elevation view of another embodiment of the invention having an interruptible fluid flow path, a retractable cannula projecting forwardly out of the housing, and a laterally slidable actuator.
Figure 5:
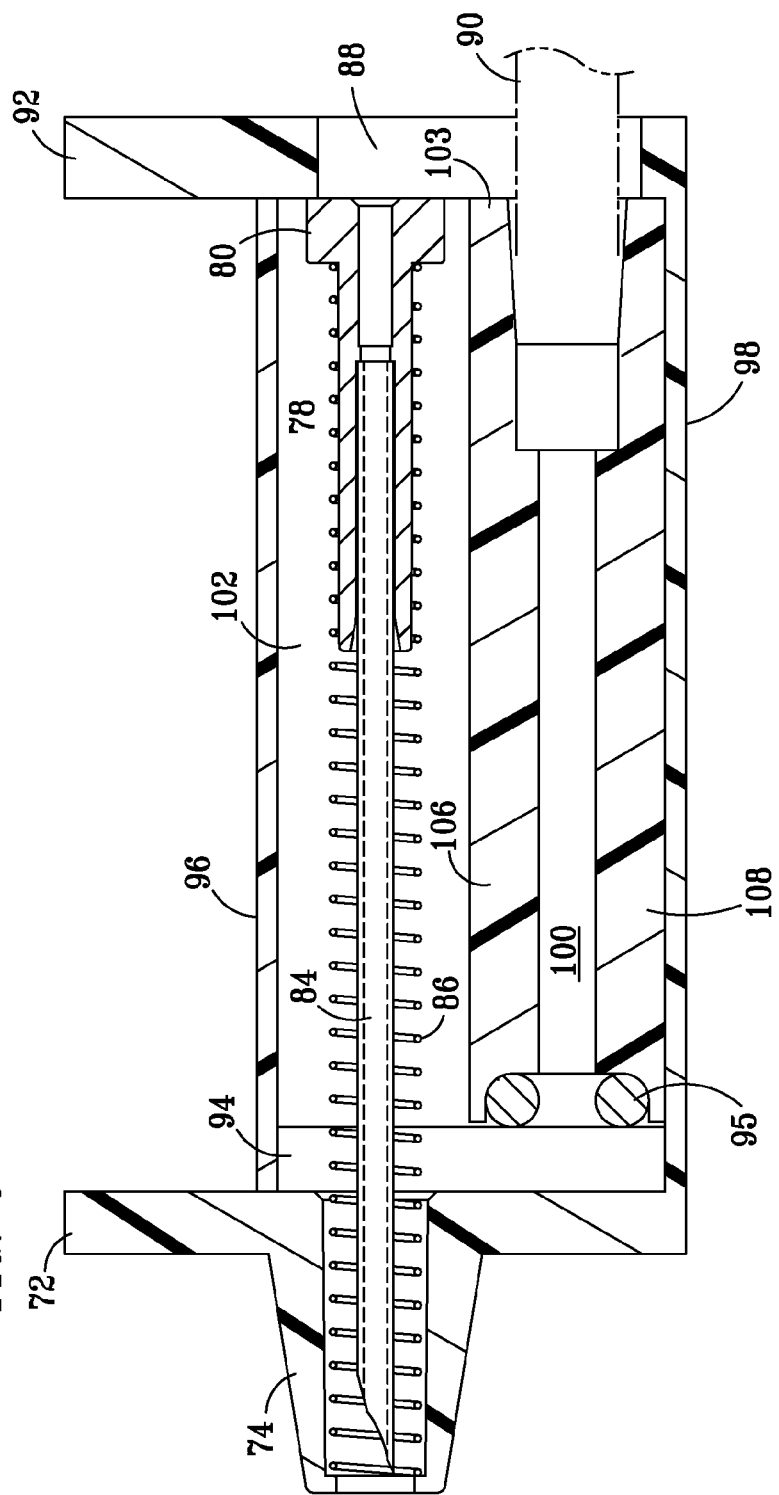
FIG. 5 is a cross-sectional front elevation view of the embodiment of FIG. 4 following interruption of the fluid flow path and retraction of the cannula into the retraction cavity.

Another embodiment of the invention is disclosed and described in relation to FIGS. 4 and 5. Referring to FIG. 4, device 70 is preferred for use as part of a blood collection apparatus or an IV infusion set. Device 70 comprises a substantially rectangular housing having front wall 72 with forwardly projecting conical nose 74; rear wall 92 with open slot 88; side wall 98; and cooperating, substantially flat bottom wall 104 and a corresponding top wall (not visible in the cross-sectional view) that interconnect walls 72, 92 and 98. The edges of bottom wall 104 and the corresponding top wall (not visible) that are opposite side wall 98 are not visible in FIG. 4, but extend between front wall 72 and back wall 92 at a point slightly beyond the side of slot 88 that is farthest removed from wall 98. Sliding track 94, seen behind front wall 72, is preferably unitarily formed as part of front wall 72.

As shown and described, the housing of device 70 defines a structure into which retraction mechanism 76 and actuator 96 are installable. Retraction mechanism 76 preferably further comprises cannula holder 78 having a larger diameter head 80, and a biasing member exerting a rearwardly directed force against cannula holder 78. A preferred biasing member is compression spring 86. Retraction mechanism 76 is installable into front wall 72, nose 74 and sliding track 94 of the housing from the rear, preferably prior to the installation of cannula 84 and actuator 96. Coil spring 86 is placed over the forwardly extending end of cannula holder 78 and cannula holder 78 is then inserted into nose 74 until the forwardly facing end of spring 86 seats against the annular shoulder inside the front opening of nose 74 that is disposed around cannula holder 78. As spring 86 is compressed, a portion of annular shoulder 82 on the forwardly facing surface of head 80 abuts against the rearwardly facing surface of front wall 72 that is adjacent to the opening through nose 74. While retraction mechanism 76 is held in place (as by temporarily clamping the portion of cannula holder 78 extending forwardly out of nose 74), actuator 96 is desirably inserted into sliding track 94 from the side of the housing opposite wall 98, and is moved laterally to a position as shown in FIG. 4 where sealing member 95 provides a fluid-tight seal permitting fluid flow between head 80 of cannula holder 78 into fluid flow path 100 of actuator 96.

Actuator 96 is preferably an elongate, substantially rectangular body made to slidably engage at least one guide or sliding track 94 on the inside of the housing to facilitate lateral movement of actuator 96 within the housing. The interior of actuator 96 preferably comprises an in-line fluid flow path 100 defined by wall sections 106, 108, and a retraction chamber 102 that is offset from cannula 84 while actuator 96 is in the use position. Resilient sealing member 95, preferably an elastomeric O-ring or another similarly effective sealing member, is disposed in a recess at the forward end of fluid flow path 100 through actuator 96, where it can provide sealing engagement with the rearwardly facing surface of enlarged head 80 of cannula holder 78. It will be observed that resilient sealing member 95 seals against fluid leakage either into or out of fluid flow path 100.

When actuator 96 is positioned as shown in FIG. 4, spring 86 is maintained in its compressed state and continuously biases cannula holder 78 in a rearward direction until such time as actuator 96 is selectively repositioned following use of device 70. Once retraction mechanism 76 and actuator 96 are installed inside the housing, the rear end of cannula 84 can be inserted into the axial bore of cannula 78 and glued or otherwise secured in place. Although not shown, a frictionally engageable, removable protective cover is desirably provided for cannula 84 following its installation in cannula holder 78.

Prior to use, device 70 is preferably connected to a fluid source or fluid receptacle by means of a flexible tubing segment 90 that is insertable into or otherwise attachable to tubing connector 103 through slot 88 by conventional means. When actuator 96 is positioned as shown in FIG. 4, a substantially linear fluid flow path is established between cannula 84 and tubing segment 90. Tubing connector 103 can be a section of the bore inside actuator 96 that is tapered slightly to receive and frictionally engage a free end of tubing segment 90, or can be configured for attachment of a tubing segment by other known means such as, for example, luer connectors, threaded connectors, clamps, adhesive, and the like. Tubing segment 90 is preferably flexible polymeric tubing of any length and material that are suitable for the intended use. When configured as shown in FIG. 4, device 70 can be used to transfer fluids from an external source to be discharged through the cannula, or can be extracted or withdrawn from an external source through the cannula and subsequently discharged from the end of tubing segment 90 that is opposite to tubing connector 103.

Following use, retraction is initiated by moving actuator 96 from its use position to its retraction position by applying manual force to actuator 96 in a direction that is substantially perpendicular to the longitudinal axis through cannula 84 and cannula holder 78. Referring to FIG. 5, as actuator 96 is moved laterally toward wall 98, fluid flow path 100 through actuator 96 is shifted laterally into a position where it is no longer opposed to head 80 of cannula holder 78. Simultaneously, head 80 is acted upon by the biasing force of compressed spring 86 to propel cannula holder 78 into retraction cavity 102 of actuator 96, thereby withdrawing cannula 84 inside the housing. To produce this result, it will be apparent that the distance between back wall 92 and the front tip of nose 74 must be sufficiently great to receive the pointed end of cannula 84 at least into nose 74. Also, the length of uncompressed spring 86 is desirably such that head 80 will be maintained a sufficient distance from the front opening of nose 74 that the tip of cannula 84 does not again protrude from the front of device 70 following retraction, particularly if device 70 is rotated to a vertical position with the cannula pointing down.

Another embodiment of the invention, in which the actuator is repositioned arcuately relative to the housing to initiate retraction, is described in relation to FIGS. 6-10. Referring first to FIGS. 6-8, medical device 110 is disclosed that comprises housing 112, actuator 114, a retraction mechanism 118, and a forwardly projecting cannula, preferably needle 122. Housing 112 further comprises a hollow body having substantially flat top and bottom surfaces, an inclined finger pad 134, a forwardly extending, open neck 136, open side and back sections including actuator stop rail 140, recessed wall section 168, and aligned, oppositely disposed apertures 126 for pivotably attaching actuator 114 to housing 112.

Actuator 114 preferably comprises actuator contact surface 132, contact surface 166, actuator positioning rail 138, outwardly projecting mounting bosses 128 insertable into mating engagement with apertures 126 of housing 112, and tubing aperture 130. Retraction mechanism 118 preferably comprises a needle holder having a forwardly extending, small diameter portion 106 and a larger-diameter head 108 disposed rearwardly of small diameter portion 106. Compression spring 116 is configured to slide over small diameter portion 106 and to abut against the forwardly facing annular surface of head 108. A sealing member, preferably O-ring 120, is further described below.

Referring to FIG. 9, the retraction mechanism is inserted into neck 136 of housing 112 from the rear, with small diameter portion 106 of the needle holder projecting forwardly through the opening in the front. Spring 116 slidably engages small diameter portion 106 and the forward end of spring 116 is seated against an annular shoulder adjacent to the front opening inside neck 136. The other end of spring 116 abuts against an annular shoulder of head 108. Spring 116 is compressed, and is maintained in the pre-retraction position by an opposing force exerted against head 108 by actuator 114. Actuator 114 is disposed in its use position relative to housing 112, with mounting bosses 128 pivotably inserted into apertures 126 and with contact surface 166 abutting against the inside surface of housing 112 that is adjacent to recessed wall section 168. Actuator 114 comprises fluid flow path 154 bounded by walls 150, 152, and retraction cavity 164. Space 124 in housing 112 is provided to receive a portion of actuator 114 when it is repositioned to terminate fluid flow and initiate retraction.

With actuator 114 in this position, fluid flow path 154 through actuator 114 is disposed in fluid communication with axial passageway 144 through the needle holder and with the inside of needle 122. Sealing member 120, seated in recess 148, desirably provides fluid-tight sealing engagement between the forward end of walls 150, 152 and head 108 of the needle holder. This sealing engagement is facilitated by an annular shoulder 146 of head 108. Tubing connector 156 desirably comprises outwardly tapering walls 142 at the rear end of fluid flow path 154 and is adapted to receive and engage an end of tubing segment 162 (shown in phantom outline). Projecting boss 158 of housing 112, located adjacent to the forwardly facing end of retraction cavity 164 is provided to prevent actuator 114 from inadvertently being moved from the pre-retraction position to the retraction position. In practice, the spacing between boss 158 and facing surface 160 of actuator 114 is desirably less than that shown for illustrative purposes in FIG. 9.

After the transfer of fluids through device 110 in either direction has been completed to the extent desired, the fluid flow is easily terminated by repositioning actuator 114 relative to housing 112 by applying pressure against actuator contact surface 132, which causes actuator 114 to pivot in the direction shown by arrow 160. Although some manual pressure is required to overcome the resistance of pushing surface 160 over boss 158 and to move sealing member 120 past head 108, the required force is desirably such that it can easily be applied by an adult user. It will again be observed that resilient sealing member 120 seals against fluid leakage either into or out of fluid flow path 154.

Figure 10:
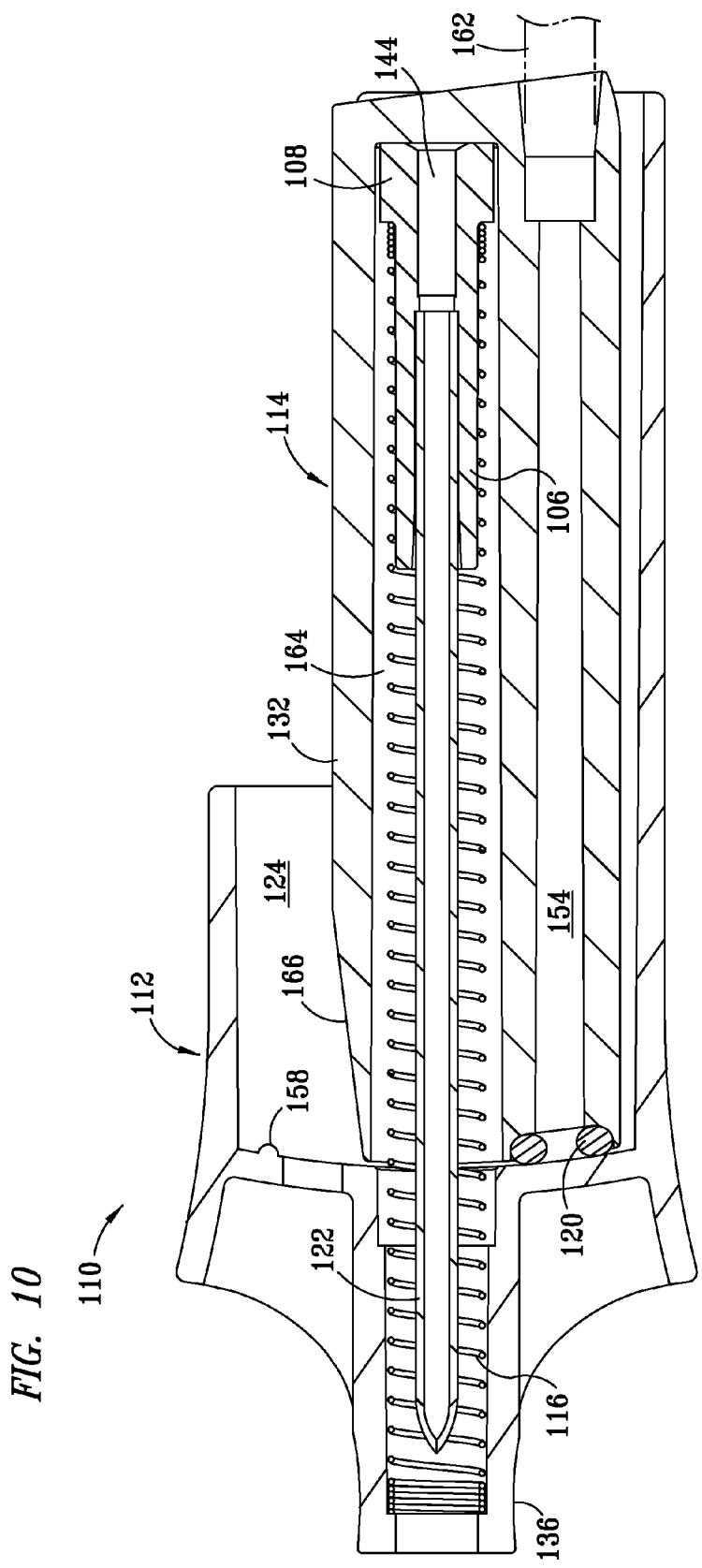
FIG. 10 is an enlarged cross-sectional plan view of the embodiment of FIG. 9 following interruption of the fluid flow path and retraction of the cannula.

Referring to FIG. 10, after actuator 114 is repositioned relative to housing 112 as shown, fluid flow between needle 122 and tubing segment 162 is blocked, fluid flow path 154 is offset from the opening through neck 136 and from passageway 144 through head 108. Furthermore, as soon as wall 150 clears head 108, retraction cavity 164 is pivoted into coaxial alignment with the opening through neck 136, and the biasing force of compressed spring 122 projects the needle holder into the retraction cavity, simultaneously withdrawing the tip of needle 122 from the patient and into housing 112 to avoid accidental needle sticks and prevent reuse of device 110.

Another embodiment of the invention is described in relation to FIGS. 11-16. This embodiment is particularly preferred for use in collecting fluids comprising gases, such as arterial blood gases, intended for subsequent analysis, and also comprises an actuator that is repositioned arcuately relative to the housing to initiate retraction. Referring first to FIGS. 11-14, medical device 200 is disclosed that comprises housing 226, actuator 204, needle holder 220, spring 222, hermetic sealing element 218 and forwardly projecting needle 224. Housing 226 further comprises a hollow body having substantially flat top and bottom surfaces 202, oppositely disposed and integrally formed finger grips with textured gripping surfaces 206, a forwardly extending, tapered neck 238 with opening 228, an open side and back, and aligned, oppositely disposed apertures 230 for pivotably attaching actuator 204 to housing 226. Protective cover 232 is desirably provided to protect needle 224 prior to use, and should be removed from needle 224 prior to use.

Actuator 204 preferably comprises actuator contact surface 234, outwardly projecting mounting bosses 212 insertable into mating engagement with apertures 230 of housing 204, retraction cavity 216, recess 214 around the opening of the fluid flow path, and a tubing connector 208 that extends rearwardly from housing 226. Referring to FIGS. 13 and 14, tubing connector 208 further comprises half of a Luer connector 236 to facilitate attachment of device 200 to another fluid source or receptacle, depending upon the intended use.

Referring to FIGS. 15-16, the retraction mechanism is installed by inserting it into axial passageway 250 through neck 238 of the housing from the rear, with small diameter portion 221 of needle holder 220 projecting forwardly through opening 228 in the front. Spring 222 slidably engages small diameter portion 221 and the forward end of spring 222 is seated against an annular shoulder 252 adjacent to front opening 228 of neck 238. The other end of spring 222 abuts against an annular shoulder of larger diameter head 223 of needle holder 220. Spring 222 is compressed, and is maintained in the pre-retraction position by an opposing force exerted against head 223 by actuator 204. Actuator 204 is disposed in its use position relative to housing 226 with mounting bosses 212 pivotably inserted into apertures 230 (FIG. 12) and with actuator contact surface 234 abutting against the inside surface of housing 226 that is underneath the nearest adjacent textured gripping surface 206. Actuator 204 comprises fluid flow path 242 and retraction cavity 216. Space 244 in housing 226 is provided to receive a portion of actuator 204 when it is repositioned to terminate fluid flow and initiate retraction.

With actuator 204 in the position shown in FIG. 15, fluid flow path 242 through actuator 204 is disposed in fluid communication with axial passageway 225 through the needle holder and with axial passageway 258 inside needle 224. Hermetic sealing member 246, seated in recess 214, desirably provides fluid-tight sealing engagement between the forward end of fluid flow path 242 and head 223 of the needle holder. Tubing connector 208 desirably comprises stepped bore 240 providing fluid communication with fluid flow path 242. Projecting boss 235 of housing 226, located adjacent to the forwardly facing end of retraction cavity 216 is provided to prevent the actuator from being moved inadvertently from the pre-retraction position to the retraction position shown in FIG. 16.

Referring to FIG. 16, after the transfer of fluids through device 200 in either direction has been completed to the extent desired, the fluid flow is easily terminated by repositioning the actuator relative to housing 226 by applying pressure against actuator contact surface 234, which causes the actuator to pivot in the direction shown by arrow 260. Although some manual pressure is required to overcome the resistance of pushing surface 237 (FIG. 15) over boss 235 and to move sealing member 246 past head 223, the required force is desirably within the range that can be applied smoothly by an adult user. After the actuator is repositioned relative to housing 112 as shown in FIG. 16, fluid flow between needle 224 and tubing connector 208 is blocked, fluid flow path 242 is offset from the opening through passageways 248, 250. Furthermore, as soon as retraction cavity 164 is pivoted into coaxial alignment with the passageways 248, 250, the biasing force of compressed spring 224 projects needle holder 221, 223 into the retraction cavity, simultaneously withdrawing the tip of needle 224 from the patient and into housing 226 to avoid accidental needle sticks and prevent reuse.

Another embodiment of the invention is described in relation to FIGS. 17-20. This embodiment, which is particularly preferred for use in extracting, collecting or infusing fluids, also comprises an actuator that is repositioned rotationally, most preferably arcuately, relative to the housing to initiate retraction. Referring first to FIGS. 17-18, medical device 300 is disclosed that comprises housing 304, actuator 316, needle holder 312, spring 310, sealing element 314 and forwardly projecting needle 308. Housing 304 further comprises a hollow body having substantially flat top and bottom surfaces, oppositely disposed and integrally formed finger grips with textured gripping surfaces 340, a forwardly extending, tapered neck 306 with a forwardly extending opening, an open side and back, and aligned, oppositely disposed apertures 324 for pivotably attaching actuator 316 to housing 304. Protective cover 302 is desirably provided to protect needle 308 prior to use, and should be removed from needle 308 prior to use.

Referring to FIGS. 18 and 19, in this embodiment of the invention, an external connector body 322 is provided that is attachable to fluid flow passage 328 through actuator 316 by means of tubing segment 318 having a length that is appropriate for attachment of another device (not shown) that is either a source of, or receptacle for, fluids to be infused into or extracted from, a patient. Referring to FIG. 19, tubing segment 318 (which can range in length, for example, from one to four feet or more) is preferably inserted into the rear of actuator 316 and glued, welded, clamped or otherwise secured in place to establish fluid communication with fluid flow path 328, and is likewise attachable to connector body 322 through an opening in nose 320, thereby establishing fluid communication with stepped axial bore 332 through connector body 322. Connector 334 at the rear of connector body 322 is desirably provided, most preferably with half of a standard Luer connector, to facilitate attachment to another device, preferably a fluid source or receptacle. The end of tubing segment inserted into nose 320 of connector body 322 is also preferably attached using an adhesive or by any other suitable conventional means. Connector body 322 can also optionally be provided with oppositely directed stabilization wings 336 if desired for use in securing connector body 322 to another surface or article.

Prior to the installation of actuator 316 inside housing 304, the retraction mechanism comprising needle holder 312 and spring 310 is preferably installed by inserting it into neck 306 of housing 304 from the rear as previously described in relation to the embodiment of FIGS. 11-17, with the smaller diameter portion of needle holder 312 projecting forwardly through the opening in the front of neck 306. Spring 310 is compressed during installation, and is maintained in the pre-retraction position by an opposing force exerted against the head of needle holder 312 by actuator 316. In FIG. 19, actuator 316 is disposed in its use position inside housing 304 as previously described for actuator 204 in relation to housing 226 of FIG. 15. Actuator 316 comprises fluid flow path 328 and retraction cavity 330. Space 326 in housing 304 is provided to receive a portion of actuator 316 when it is repositioned to terminate fluid flow and initiate retraction.

With actuator 316 in the position shown in FIG. 19, fluid flow path 328 through actuator 316 is disposed in fluid communication with axial passageway through needle holder 312 and with the axial passageway 258 inside needle 308. Elastomeric sealing member 314 desirably provides fluid-tight sealing engagement between the forward end of fluid flow path 328 and the head of needle holder 312. The rear portion of fluid flow path 328 desirably comprises tapering walls to receive and engage an end of tubing segment 318 as previously described. A projecting boss as previously described in relation to boss 235 of housing 226 of FIG. 15 is desirably located adjacent to the forwardly facing end of retraction cavity 330 to prevent actuator 316 from being moved inadvertently from the pre-retraction position of FIG. 19 to the retraction position shown in FIG. 20.

Referring to FIG. 20, after the transfer of fluids through device 300 in either direction has been completed to the extent desired, the fluid flow is easily terminated by repositioning actuator 316 relative to housing 304 by applying pressure against the actuator contact surface as indicated by arrow 338, which causes actuator 316 to pivot in the direction shown by arrow 338. After the actuator is repositioned relative to housing 304 as shown in FIG. 20, fluid flow between needle 308 and tubing connector body 322 is blocked, and fluid flow path 328 is offset from the opening through nose 306. Furthermore, as soon as retraction cavity 330 is pivoted into coaxial alignment with the opening through neck 306 of housing 304, the biasing force of compressed spring 308 forces needle holder 312 into retraction cavity 330, simultaneously withdrawing the tip of needle 308 from the patient and into housing 304 to avoid accidental needlesticks and prevent reuse, thereby reducing the related potential for spreading fluid-borne pathogens to another person.

As disclosed herein, all housings, actuators, cannula holders, protective covers, end caps and tubing connectors can be made of any suitable material such as, for example, plastic, metal, ceramic, glass, or the like. For medical application such as IV infusion and blood collection, the use of molded polypropylene is preferred. Similarly, depending upon the intended use or application, cannulas suitable for use in the invention can be made of metal, plastic or ceramic materials, with metal being preferred. Resilient parts used as fluid sealing members or cannula holder plugs are desirably made of rubber, other elastomeric polymers, or rubber-modified plastic.

When using the devices disclosed in relation to FIGS. 1-5, and assuming that the housing is maintained in a stationary position during retraction, a tubing segment connected to the rear of the device is not moved axially, laterally or directionally when the actuator is repositioned to terminate the fluid flow and withdraw the cannula into the housing. When using the devices of FIGS. 6-20, wherein flow is terminated and the cannula is retracted by arcuate repositioning of the actuator as it pivots relative to the housing, the axial, lateral and directional movements of an attached tubing segment are slight compared to the travel distance previously associated with the use of conventional devices.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

a housing;
a cannula;

What is claimed is:

1. A device comprising:
    a connector attachable to a fluid source or a receptacle external to the device;
    a fluid flow path in fluid communication with the connector;
    a retraction mechanism biasing the cannula rearwardly;
    a retraction cavity having a front portion, wherein the retraction cavity is connected to the housing such that at least the front portion of the retraction cavity can move laterally from a first position to a second position, and wherein the retraction mechanism is separate from and not coaxial with the fluid flow path;
    wherein when the front portion of the retraction cavity is in the first position, the cannula projects forwardly from the housing, the cannula is in fluid communication with the connector through the fluid flow path, and the retraction cavity is not coaxial to or aligned with the cannula;
    wherein when the front portion of the retraction cavity is in the second position, the front portion of the retraction cavity is aligned with the cannula and the retraction mechanism retracts the cannula into the retraction cavity such that the cannula no longer projects forwardly from the housing and the cannula is no longer in fluid communication with the connector.

2. The device of claim 1 further comprising at least one sealing element configured to prevent fluid leakage into or out of the fluid flow path.

3. The device of claim 1 wherein at least a portion of the retraction activity is slidably disposed within the housing.

4. The device of claim 1 wherein the retraction cavity is pivotally connected to the housing.

5. The device of claim 1 wherein the fluid flow path is substantially parallel to the retraction cavity.

6. The device of claim 1 wherein the entire retraction cavity is moved laterally to move the front portion from the first to the second portion.

* * * * *

UNITED STATES PATENT AND TRADEMARK OFFICE
CERTIFICATE OF CORRECTION

PATENT NO. : 9,440,033 B2
APPLICATION NO. : 13/902564
DATED : September 13, 2016
INVENTOR(S) : Thomas J. Shaw et al.

It is certified that error appears in the above-identified patent and that said Letters Patent is hereby corrected as shown below:

In the Claims

Column 14, Line 32, "activity" in Claim 3 should read --cavity--.

Signed and Sealed this
Third Day of January, 2017

Michelle K. Lee
*Director of the United States Patent and Trademark Office*